(12) United States Patent
Tandon et al.

(10) Patent No.: US 10,149,618 B1
(45) Date of Patent: Dec. 11, 2018

(54) SUBDURAL ELECTRODE LOCALIZATION AND VISUALIZATION USING PARCELLATED, MANIPULABLE CEREBRAL MESH MODELS

(71) Applicant: Board of Regents, the University of Texas System, Austin, TX (US)

(72) Inventors: Nitin Tandon, Houston, TX (US); Christopher R. Conner, Houston, TX (US); Thomas A. Pieters, Houston, TX (US); Cihan Mehmet Kadipasaoglu, Houston, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 662 days.

(21) Appl. No.: 14/656,117

(22) Filed: Mar. 12, 2015

Related U.S. Application Data

(60) Provisional application No. 61/951,861, filed on Mar. 12, 2014.

(51) Int. Cl.
| | |
|---|---|
| *A61B 5/05* | (2006.01) |
| *A61B 5/00* | (2006.01) |
| *A61B 5/055* | (2006.01) |
| *A61B 6/03* | (2006.01) |
| *A61B 6/00* | (2006.01) |
| *A61B 5/0476* | (2006.01) |

(52) U.S. Cl.
CPC .......... *A61B 5/0042* (2013.01); *A61B 5/0037* (2013.01); *A61B 5/0077* (2013.01);
(Continued)

(58) Field of Classification Search
None
See application file for complete search history.

(56) References Cited

U.S. PATENT DOCUMENTS

| | | |
|---|---|---|
| 2014/0094836 A1 | 4/2014 | Feng et al. |
| 2014/0276007 A1 | 9/2014 | Sela et al. |
| 2015/0025526 A1 | 1/2015 | Hua et al. |

FOREIGN PATENT DOCUMENTS

| | | |
|---|---|---|
| EP | 2716242 A1 | 4/2014 |
| EP | 2829249 A1 | 1/2015 |
| | (Continued) | |

OTHER PUBLICATIONS

Rodionov et al., "Feasibility of multimodal 3D neuroimaging to guide implantation of intracranial EEG electrodes". Aug. 14, 2013. Epilepsy Research(2013) 107, pp. 91-100.*

(Continued)

*Primary Examiner* — James Kish
(74) *Attorney, Agent, or Firm* — Paker Highlander PLLC

(57) ABSTRACT

This invention relates generally to methods for localization and visualization of implanted electrodes and penetrating probes in the brain in 3D space with consideration of functional brain anatomy. Particularly, this invention relates to precise and sophisticated methods of localizing and visualizing implanted electrodes to the cortical surface and/or topological volumes of a patient's brain using 3D modeling, and more particularly to methods of accurately mapping implanted electrodes to the cortical topology and/or associated topological volumes of a patient's brain, such as, for example, by utilizing recursive grid partitioning on a manipulable virtual replicate of a patient's brain. This invention further relates to methods of surgical intervention utilizing accurate cortical surface modeling and/or topological volume modeling of a patient's brain for targeted placement of electrodes and/or utilization thereof for surgical intervention in the placement of catheters or other probes into it.

18 Claims, 6 Drawing Sheets

(52) U.S. Cl.
CPC ............ *A61B 5/0476* (2013.01); *A61B 5/055* (2013.01); *A61B 6/032* (2013.01); *A61B 6/4417* (2013.01); *A61B 6/5205* (2013.01)

(56) References Cited

FOREIGN PATENT DOCUMENTS

| WO | WO 2012/163083 | 5/2012 |
|---|---|---|
| WO | WO 2013/139178 | 3/2013 |
| WO | WO 2014/101298 | 12/2013 |
| WO | WO 2014/138914 | 3/2014 |
| WO | WO 2014/138915 | 3/2014 |
| WO | WO 2014/138923 | 3/2014 |
| WO | WO 2014/138916 | 9/2014 |
| WO | WO 2014/138997 | 9/2014 |
| WO | WO 2014/139009 | 9/2014 |
| WO | WO 2014/139010 | 9/2014 |
| WO | WO 2014/139018 | 9/2014 |
| WO | WO 2014/139019 | 9/2014 |
| WO | WO 2014/139020 | 9/2014 |
| WO | WO 2014/139021 | 9/2014 |
| WO | WO 2014/139022 | 9/2014 |
| WO | WO 2014/139023 | 9/2014 |
| WO | WO 2014/139024 | 9/2014 |
| WO | WO 2015/003271 | 1/2015 |
| WO | WO 2015/040473 | 3/2015 |

OTHER PUBLICATIONS

Princich et al., "Rapid and efficient localization of depth electrodes and cortical labeling using free and open source medical software in epilepsy surgery candidates". Frontiers in Neuroscience, Dec. 2013, vol. 7, Article 260. pp. 1-8.*

Taimouri et al., "Electrode Localization for Planning Surgical Resection of the Epileptogenic Zone in Pediatric Epilepsy." Int J Comput Assist Radiol Surg. Jan. 2014 ; 9(1): pp. 91-105.*

LaViolette et al. "Three-Dimensional Visualization of Subdural Electrodes for Presurgical Planning." Neurosurgery. Mar. 2011 ; 68(1 0 0): pp. 152-161.*

Hewitt, John. "3D-printed charred micro bunny electrodes for brain stimulation". Jun. 4, 2013. ExtremeTech. pp. 1-2. Found online at: https://www.extremetech.com/extreme/157254-3d-printed-charred-micro-bunny-electrodes-for-brain-stimulation.*

"BrightMatter™ Plan: It's all Part of the Plan," *BrightMatter™ Neurosurgical Solutions*. Synaptive Medical. Available online at: http:// http://www.synaptivemedical.com/plan/, retrieved Jun. 18, 2015.

Dykstra et al., "Individualized localization and cortical surface-based registration of intracranial electrodes," *NeuroImage*, 59:3563-3570, 2012.

Hermes et al., "Automated electrocorticographic electrode localization on individually rendered brain surfaces," *Journal of Neuroscience Methods*, 185:293-298, 2010.

Keenan, Joseph. "Synaptive's 'GPS for the brain' gets FDA green light," *FierceMedicalDevices*. FierceMarkets, a division of Questex Media Group LLC, Available online at: http://www.fiercemedicaldevices.com/story/synaptives-gps-brain-gets-fda-green-light/2015-04-09, retrieved Jun. 18, 2015.

Rodionov et al., "Feasibility of multimodal 3D neuroimaging to guide implantation of intracranial EEG electrodes," *Epilepsy Research*, 107:91-100, 2013.

Yang et al., "Localization of dense intracranial electrode arrays using magnetic resonance imaging," *NeuroImage*, 63:157-165, 2012.

* cited by examiner

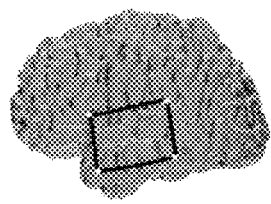 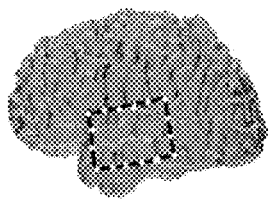 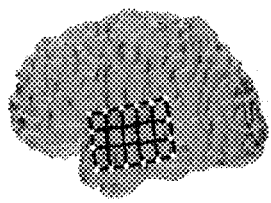 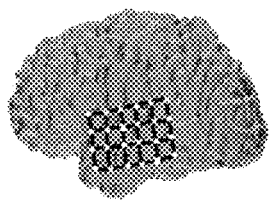
*Fig.4a.*　　*Fig.4b.*　　*Fig.4c.*　　*Fig.4d.*
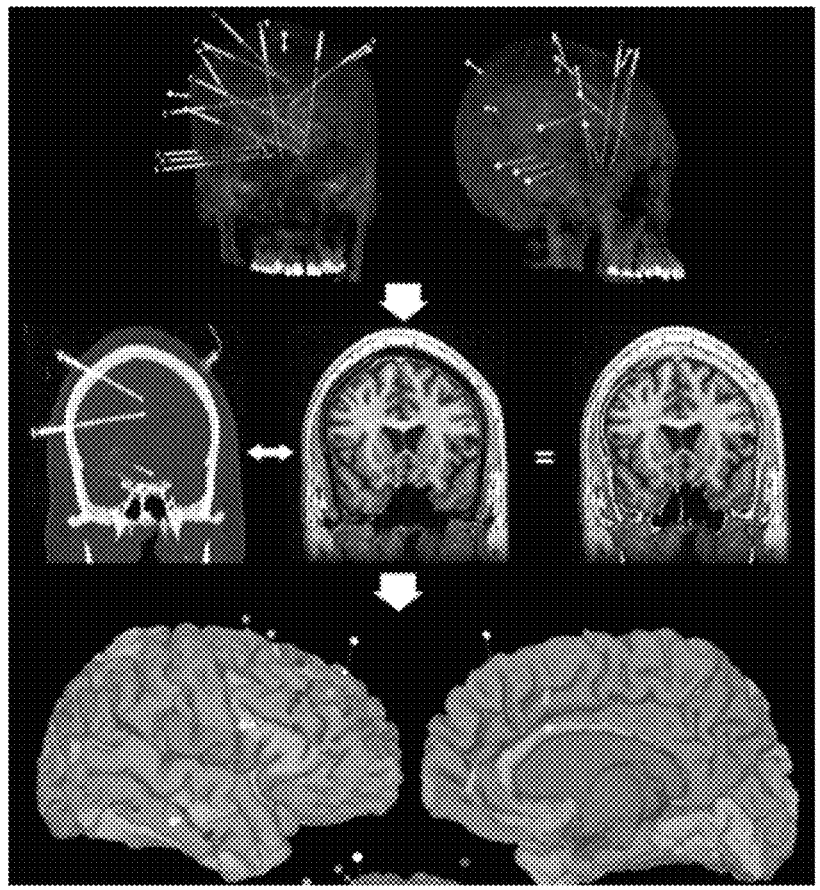
*Fig.5a.*
*Fig.5b.*
*Fig.5c.*

SUBDURAL ELECTRODE LOCALIZATION AND VISUALIZATION USING PARCELLATED, MANIPULABLE CEREBRAL MESH MODELS

CROSS-REFERENCE TO RELATED APPLICATIONS

This application claims the benefit and priority of U.S. provisional patent application Ser. No. 61/951,861, filed Mar. 12, 2014, entitled "Subdural Electrode Localization and Visualization Using Parcellated, Manipulable Cerebral Mesh Models", the contents of which is hereby incorporated by reference in its entirety.

STATEMENT UNDER 35 U.S.C. § 202(C)(6)

These inventions were made with U.S. Government support under Grant Nos. RR024149 and RR024148 awarded by the National Institutes of Health. The government has certain rights in the invention.

COPYRIGHT NOTICE

A portion of the disclosure of this patent document contains material that is subject to copyright protection. The copyright owner has no objection to the facsimile reproduction by anyone of the patent document or the patent disclosure, as it appears in the U.S. Patent and Trademark Office patent file or records, but otherwise reserves all copyright rights whatsoever.

FIELD OF THE INVENTION

This invention relates generally to methods for localization and visualization of implanted electrodes and penetrating probes in the brain. Particularly, this invention relates to precise and sophisticated methods of localizing and visualizing implanted electrodes to the cortical surface and/or topological volumes of a patient's brain, and more particularly to methods of accurately mapping implanted electrodes to the cortical topology and/or associated topological volumes of a patient's brain, such as, for example, by utilizing recursive grid partitioning on a manipulable virtual replicate of a patient's brain. This invention further relates to methods for guiding surgical intervention utilizing accurate cortical surface modeling and/or topological volume modeling of a patient's brain for targeted placement of electrodes and/or utilization thereof for surgical intervention in the placement of catheters or other probes into it.

BACKGROUND OF THE INVENTION

Currently, medically intractable epilepsy afflicts about 1 million Americans. Unfortunately, most of the cases do not have a well definable focus, where the surgical removal of which could possibly eliminate the seizures. Implantation of subdural electrodes (SDEs) or depth electrodes (DEs) in patients with pharmaco-resistant epilepsy is a common strategy in epilepsy surgery and therapy that is employed when there is no discrete electro-physiologically abnormal lesion.

A central issue that occurs after implantation of the SDEs is the non-linear deformation of the brain surface by mass effect of the SDE array and due to the blood and fluid accumulation underneath the craniotomy flap used for the SDE implantation, as is seen on post-operative computed tomography (CT) scans, such as due to the blood and fluid accumulation underneath the craniotomy flap used for the SDE implantation. The deformation affects the localization of all electrodes, especially those under the bone flap, and causes them to appear to be depressed beneath the surface of the brain when visualized in a model created using co-registration of the post-implantation MRI scan with the a pre-implantation anatomical magnetic resonance imaging (MRI). As a result, some of the implanted electrodes may appear incorrectly in the model as being "buried" inside the brain rather than on the brain surface. Because the electrodes lying beyond the craniotomy flap are much less affected by this distortion problem, the unequal shift (displacement of the SDEs) renders inaccurate the localization based on mutual cost information algorithms that co-register the post-implant CT with the pre-implant MRI.

Attempts have been made to correct the displacement of the SDEs using semi-automated techniques to project "displaced" SDEs onto a high resolution MRI scan of the same patient. However, a significant error still exists with the current techniques for electrode localization. This error can be up to an 8 mm maximum error for a given electrode and a 4 mm mean error for all SDEs in a given individual. Given that the inter-electrode distance is usually 10 mm, an error of even 4 mm is substantial, and could possibly cause the electrode to be localized on an incorrect gyms, or even worse, an incorrect lobe.

The placement of DEs for localization of epilepsy was principally focused in years past only on limbic structures (hippocampus, amygdala and entorhinal cortex). Over the past few years the practice of stereo-electroencephalography (SEEG)—which involves the practice of placement of multiple (typically 8-16) DEs into myriad cortical and limbic targets in the brain has gained broader adoption. In its classical implementation this approach (designed in France in the 1960s) is performed using strictly orthogonal (lateral-to-medial) trajectories based on an arteriogram and using a stereotactic head frame. The limitation of this is that only certain trajectories can be accomplished and it is time consuming. The availability of three-dimensional frameless and frame based stereotactic navigation systems allow for the placement of these electrodes along azimuth-based trajectories. Such multi-directional trajectories allow for the placement of electrodes into any cortical structure. However, at the current time there are no good strategies to optimize the placement of these electrodes into "MRI-normal" or apparently non-lesional tissues that can generate seizures but are not abnormal on imaging. A "best-guess" approach is used by surgeons who place these electrodes, and who use approximations rather than patient specific anatomico-physiological boundaries.

SUMMARY OF THE INVENTION

The present invention relates to methods for localization and visualization of implanted electrodes, such as, for example, subdural electrodes (SDEs) and depth electrodes (DEs), particularly to localizing and visualizing implanted electrodes to the cortical surface and/or particular volumes of a patient's brain, and more particularly to methods of accurately mapping implanted electrodes to the cortical topology and/or associated topological volumes of a patient's brain. This invention further relates to methods of surgical intervention utilizing accurate cortical surface modeling and/or topological volume modeling of a patient's brain for placement of electrodes and/or utilization thereof for surgical intervention, such as for accurately placing electrodes for optimal recording of electrical signals and/or properly identifying sites for surgical intervention.

In general, accurate and precise localization of electrodes is essential for the interpretation of data from intracranial electro-corticographic (ECoG) recordings. Various physiological issues, such as, for example, blood and fluid accumulation underneath the craniotomy flap, may lead to a non-linear deformation of the brain surface and of an electrode array on post-operative CT scans, and may adversely impact the accurate localization of electrodes located underneath the craniotomy. Prior methods that localize electrodes based on their identification on a post-implantation CT, with co-registration to a pre-implant MRI may further result in significant problems with accuracy of the electrode localization.

The precise localization of implanted electrodes is also generally essential both for clinical purposes as well as for research purposes, such as, for example, in integrating estimates from other imaging data sets like fMRI, PET, SPECT and/or MEG. Additionally, the growing field of neural prosthetics also depends very greatly on precise estimates of where in the brain data is being collected from, or where stimulation for neuromodulation is being delivered.

In general as disclosed herein, precise localization as well as optimized viewing of implanted intracranial electrodes may be shown on a manipulable 3D cortical mesh model that may be parcellated, such as by automatic manipulation, to show anatomic details of specific brain regions (e.g. specific cortical gyri, functional zones), such as where the electrodes are placed. Thus, both precise localization as well as optimized viewing of implanted intracranial electrodes may be accomplished. For example, the mesh model may be morphed into unnatural shapes, such as, for example, a dilated, smoothed pial surface, that may allow for viewing the areas that individual electrodes are in contact with, as well as the regions where such recording/stimulation is not happening, thus providing a holistic view of the data. Further, the localization of electrodes onto an individually parcellated cortical surface may allow for the a priori assignment of putative functional zones relative to each electrode. This may, for example, augment, verify or altogether replace imaging based functional mapping techniques (e.g. MEG or fMRI) in some cases, and/or electrical cortical stimulation mapping in others.

Further in general, more holistic representations of the brain may be utilized, such as, for example, to illustrate relationships at electrodes to the entire cortex, including "buried" or "unburied" surface features. For example, it is generally known that subdural grid electrodes only sample from gyral crowns and not from the intervening sulci or from buried cortex such as the insula. The pial mesh model of the brain may thus be morphed into a "lissencephalic" view of the entire cortex. This process essentially flattens the difference between the depths of the sulci and the peaks of the gyri, while still preserving the overall shape of the brain. This may generally allow visualization of electrodes, such as for example, particularly depth electrodes (DEs), which may otherwise be buried inside a sulcus.

In one aspect of the present invention, a method for localization and/or visualization of implanted electrodes on a patient's brain includes utilizing visual registration of electrodes in relation to anatomical features, such as, for example, cortical surface anatomy. In general, a three-dimensional (3D) cortical model of the patient's brain may be generated, such as by utilizing an anatomical magnetic resonance imaging (MRI) study, and/or any other appropriate method. The 3D cortical model of the patient's brain may further generally include gyral and sulcal anatomical features of the brain, parcellation and visual representation of individual features, and/or any other desired anatomical features which may be included with a particular scanning and/or imaging method, such as discussed in general above.

In some exemplary embodiments, the visual registration of implanted electrodes may utilize pre-implantation and post-implantation imaging of the brain in an electrode array implantation, such as by utilizing digital and/or analog photography of the operative site in an operating room (OR). Pre-implantation imaging may generally provide visual information of the underlying cortical surface prior to implantation of the electrodes and may thus be utilized to compare anatomical features with the 3D cortical model, such as to establish anatomical landmarks. After implantation of the electrodes, post-implantation imaging may be performed to visualize the electrodes and the anatomical features of the brain. In one embodiment, a skilled practitioner, such as, for example, a physician or veterinarian, may readily compare the anatomical features from the intraoperative imaging to the 3D cortical model, such as by matching and/or aligning anatomical landmarks, to visually translate the locations of the electrodes from the intraoperative imaging to the 3D cortical model. The localization of the electrodes on the 3D cortical model may then be employed to determine useful electrocorticographic (ECoG) information from the patient.

In another aspect of the present invention, a method for localization and/or visualization of implanted electrodes on a patient's brain includes utilizing visual registration of a set of electrodes in relation to anatomical features, such as, for example, cortical surface anatomy, and utilizing modeling to recursively determine the locations of the remaining electrodes relative to the anatomical features. In general, a three-dimensional (3D) cortical model of the patient's brain may be generated, such as by utilizing an anatomical magnetic resonance imaging (MRI) study, and/or any other appropriate method. The 3D cortical model of the patient's brain may further generally include gyral and sulcal anatomical features of the brain, parcellation and visual representation of individual features, and/or any other desired anatomical features which may be included with a particular scanning and/or imaging method, such as discussed in general above. A further 3D model may also be generated which may generally omit the sulcal anatomical features, thus omitting the "buried" portion of the cortical surface from the model. This "smoothed" 3D model may be utilized, for example, to aid in recursively registering the locations of the electrodes on the unburied cortical surface.

In some exemplary embodiments, the visual registration of a set of implanted electrodes may utilize pre-implantation and post-implantation imaging of the brain in an electrode array implantation, such as by utilizing digital and/or analog photography of the operative site in an OR. Pre-implantation imaging may generally provide visual information of the underlying cortical surface prior to implantation of the electrodes and may thus be utilized to compare anatomical features with the 3D model, such as to establish anatomical landmarks. After implantation of the electrodes, post-implantation imaging may be performed to visualize the electrodes and the anatomical features of the brain. In one embodiment, a skilled practitioner, such as, for example, a physician or veterinarian, may readily compare the anatomical features from the intraoperative imaging to the 3D model, such as by matching and/or aligning anatomical landmarks, to visually translate the locations of the electrodes from the intraoperative imaging to the 3D model.

In some embodiments, the electrodes may generally be implanted as a grid of electrodes with predetermined locations and/or dimensions on a substrate such that only a set of the electrodes may need to be localized and the remaining electrodes may be localized by extrapolating based on distance and/or relative position from the known electrodes. For example, a grid of electrodes may be present on a substrate in a square grid pattern with known dimensions and distance between grid points.

In some exemplary embodiments, the corner electrodes of a grid may be visually registered via intraoperative imaging, as discussed above, and then utilized to recursively localize the remaining electrodes to the cortical surface by partitioning the grid ("recursive grid partitioning"). In one embodiment, the corner electrodes may generally be present close to the boundaries of the craniotomy flap and visually registered to a smoothed 3D model, such as a 3D pial surface model which may generally omit the sulcal buried portions of the cortical surface. This may be desirable as the electrodes may generally only be implanted onto the surface unburied portions and the intervening substrate of the electrode grid may conform to the unburied contours of the pial surface, but not to the buried contours of the cortical surface. Utilizing modeling methods, the known inter-electrode distances between the corner electrodes may then be contoured to the non-linear pial surface in the smoothed 3D model and the remaining electrodes may be localized along the contoured lines. Thus the entire electrode grid may be contoured onto the smoothed 3D model to recursively yield the localized electrodes on the pial surface. This may be particularly desirable to localize electrodes which are not readily visible, such as those placed beyond the craniotomy flap, as their locations may be recursively determined using visible electrodes within the craniotomy flap region. The localization of the electrodes on the smoothed 3D model may then be aligned with the unsmoothed 3D cortical model to map the electrodes to determine useful ECoG information from the patient.

In general, other grid patterns besides square grids may also be utilized where a finite set of points in the grid may be utilized deterministically to extrapolate the other points of the grid once contoured to a 3D surface model.

In yet another aspect of the present invention, implanted DEs and electrical signals recorded by them may be mapped to a parcellated 3D model of the brain to more accurately determine the particular region(s) of the patient's brain contributing to a particular signal at a DE and/or a portion thereof. In some exemplary embodiments, imaging may be employed prior to implantation of DEs to generate the 3D model of the brain, followed by imaging after implantation of the DEs. The pre-implantation and post-implantation imaging may then be co-registered to localize the DEs in the 3D model of the brain volume, which may then be utilized to show interactions between the DEs and surrounding regions of the brain, such as by using parcellated views of the 3D model. For example, depending on the angle and location of insertion, a DE may interact with multiple distinct anatomical formations that may be visualized with the parcellated 3D model. Other anatomical formations or related information may also be included in the 3D model, such as, for example, surface and/or deep blood vessels, white matter pathways, tractography data regarding neural tracts, and/or any other desirable anatomical formations or related information.

In still another aspect of the present invention, electrical signals from implanted electrodes may be mapped to the 3D cortical surface to more accurately determine the particular region(s) of the patient's brain contributing to a particular signal at an electrode. These electrical signals may reflect normal ongoing brain activity, activity stimulated by certain normal behaviors (e.g. movement, language) or pathological activity such as seen in epilepsy. In general, traditional methods typically map electrical activity at an electrode to regions of the brain that are closest in Euclidian distance to the electrode which, without being bound to any particular theory, may erroneously attribute electrical activity to topologically distant portions of the brain due to the Euclidian distance not accounting for surrounding topology about the electrode.

In some exemplary embodiments, signal activity from implanted SDEs may be represented on a 3D cortical model to illustrate regions that may be contributing to the activity utilizing methods that account for surrounding topology around the SDEs. In general, the folded nature of the cortical surface may contribute to falsely contributing activity at an SDE to topologically distant regions, which may be distinct anatomical structures despite being situated close in Euclidian space. To aid accounting for the underlying topology of the brain surrounding an SDE, the recording area around the electrode may be projected geodesically onto the surface 3D cortical model such that buried portions of the cortical surface are accounted for in attributing a region to activity at the SDE. The geodesic projection may further incorporate any desirable decay function to represent the activity signal from the recording area of the SDE.

In another aspect of the present invention, various forms of 3D modeling of the cortical surface may be utilized to guide placement of electrodes and/or to generate customized electrode arrays. In some embodiments, a 3D cortical model may be utilized to guide the location and/or orientation of electrodes, such as in arrays, such as to optimize particular desired recording regions of electrodes over areas of interest. In still other embodiments, 3D cortical models may be utilized to guide placement of an electrode array using a smaller craniotomy opening. In yet other embodiments, customized electrode arrays may be designed to conform to the particular anatomical features and/or needs for a patient by utilizing the patient's specific 3D cortical model prior to any electrode implantation.

Exemplary embodiments include a method for localization of implanted electrodes in a brain of a subject, the method comprising: performing an anatomical scan of the brain; generating a three-dimensional (3D) model of the brain using the anatomical scan, the 3D model comprising cortical topological features; performing a first direct imaging of at least a portion of a pial surface of the brain; identifying at least one anatomical landmark on the pial surface from the first direct imaging and performing a correlation of the at least one anatomical landmark to the 3D model; implanting at least one reference electrode onto the at least a portion of the pial surface of the brain; performing a second direct imaging of the at least a portion of the pial surface of the brain after the implanting; and visually localizing the at least one reference electrode on the 3D model using the correlation of the at least one anatomical landmark.

In certain embodiments, first and second direct imaging comprises an imaging method selected from the group consisting of digital photography and analog photography. In particular embodiments, the anatomical scan comprises anatomical magnetic resonance imaging (aMRI). Some embodiments further comprise implanting an array of electrodes onto the at least a portion of the pial surface of the animal brain prior to the second direct imaging, where the at least one reference electrode comprises a member of the array of electrodes. Specific embodiments further comprise visually localizing the array of electrodes on the 3D model using the correlation of the at least one anatomical landmark.

In certain embodiments, the array of electrodes are visually localized by a human medical practitioner or automatically by a computer. Particular embodiments further comprise recursively localizing the array of electrodes on the 3D model by contouring the array of electrodes to the cortical topological features in the 3D model relative to the at least one localized reference electrode, the array of electrodes comprising a grid which conforms to the pial surface in situ with the electrodes placed at known positions relative to the at least one reference electrode. In some embodiments, the array of electrodes comprises at least four reference electrodes. In specific embodiments, at least four reference electrodes are selected from the array of electrodes at positions proximal to a craniotomy boundary used to access the brain. In certain embodiments, the array of electrodes extends beyond the craniotomy boundary. In particular embodiments, the contouring of the array of electrodes to the cortical topological features comprises contouring the array of electrodes to a smoothed 3D model which omits sulcal anatomy and which is aligned with the 3D model.

Exemplary embodiments include a method for localization of implanted depth electrodes (DE) in a brain of a subject, the method comprising: performing a first anatomical scan of the brain; generating a three-dimensional (3D) model of the brain using the anatomical scan, the 3D model comprising cortical topological features; implanting at least one DE into the brain; performing a second anatomical scan of the brain after the implanting, the second anatomical scan elucidating the position and orientation of the at least one DE relative to the animal brain; aligning the first and second anatomical scans; and visually projecting the position and orientation of the at least one DE on the 3D model using aligning of the first and second anatomical scans.

In certain embodiments, the first and second anatomical scans are each performed with a scanning modality selected from the group consisting of magnetic resonance imaging (MRI), computerized tomography (CT), and a combination thereof. Particular embodiments further comprise highlighting the cortical topological features by parcellation with different visual coding in the 3D model to illustrate interactions of the DE with the cortical topological features. Some embodiments further comprise co-registering and depicting the 3D model with additional anatomical information selected from the group consisting of surface blood vessels, deep blood vessels, white matter pathways and tractography data.

Exemplary embodiments include a method of localizing recorded electrical activity from an implanted electrode comprising: localizing a position of an implanted electrode on a pial surface of a brain of a subject on a three-dimensional (3D) model of the brain generated using an anatomical scan, the 3D model comprising cortical topological features; recording electrical activity from the implanted electrode; generating a recording zone for the implanted electrode by geodesic expansion along the cortical topological features in the 3D model centered on the implanted electrode; and visualizing the electrical activity by projecting onto the recording zone on the 3D model to illustrate a potential region of the animal brain contributing to the electrical activity.

Certain embodiments further comprise generating a lissencephalic view of the 3D model by flattening a difference between depths of sulci and peaks of gyri while preserving the overall shape of the brain and projecting the recording zone onto the lissencephalic view of the 3D model. Particular embodiments further comprise highlighting the cortical topological features to generate a parcellated view with different visual coding in the 3D model and projecting the recording zone onto the parcellated view of the 3D model. Some embodiments further comprise highlighting the cortical topological features in the lissencephalic view to generate a parcellated lissencephalic view with different visual coding of the 3D model and projecting the recording zone onto the parcellated lissencephalic view of the 3D model. Specific embodiments further comprise highlighting regions of the brain not being recorded by the implanted electrode based on the outer boundaries of the recording zone of the implanted electrode. In certain embodiments, the projecting of the electrical activity comprises applying an electrical signal decay function to the geodesic expansion.

In addition to the localization of anatomical and physiological activity relative to electrode placements, the methods described herein may also be extended to the understanding of how white matter pathways (brain fiber paths) interact with these electrodes. The optimal placement of these electrodes to stimulate, lesion or modulate activity in the cortex, subcortical regions, white matter pathways may all be optimized using the approaches described herein for the placement and the visualization of DEs.

A further extension of the methods described herein is in the placement of probes for sampling or instilling biological materials, neurochemicals, or other physical or chemical materials into the cortex, the subcortical structures or the white matter pathways of the brain. The same processes as described herein can be implemented to accomplish process including but not limited to micro-dialysis, convection enhanced delivery, biopsies, delivery of nanotechnology devices, biologic materials including but not limited to drugs, stem cells and gene therapies. These various processes would benefit from the same improved precision in placement of the desired agent/sample in proximity to the desired region of interest.

The present invention together with the above and other advantages may best be understood from the following detailed description of the embodiments of the invention and as illustrated in the drawings. The following description, while indicating various embodiments of the invention and numerous specific details thereof, is given by way of illustration and not of limitation. Many substitutions, modifications, additions or rearrangements may be made within the scope of the invention, and the invention includes all such substitutions, modifications, additions or rearrangements.

BRIEF DESCRIPTION OF THE FIGURES

The drawings accompanying and forming part of this specification are included to depict certain aspects of the invention. A clearer impression of the invention, and of the components and operation of systems provided with the invention, will become more readily apparent by referring to the exemplary, and therefore non-limiting, embodiments illustrated in the drawings, wherein identical reference numerals designate the same components. Note that the features illustrated in the drawings are not necessarily drawn to scale.

FIGS. 4a, 4b, 4c and 4d illustrate a visualization of an example of recursive grid partitioning;

FIGS. 5a, 5b and 5c illustrate an example of localization of DEs onto a cortical surface map;

DETAILED DESCRIPTION OF THE INVENTION

Figure 1:
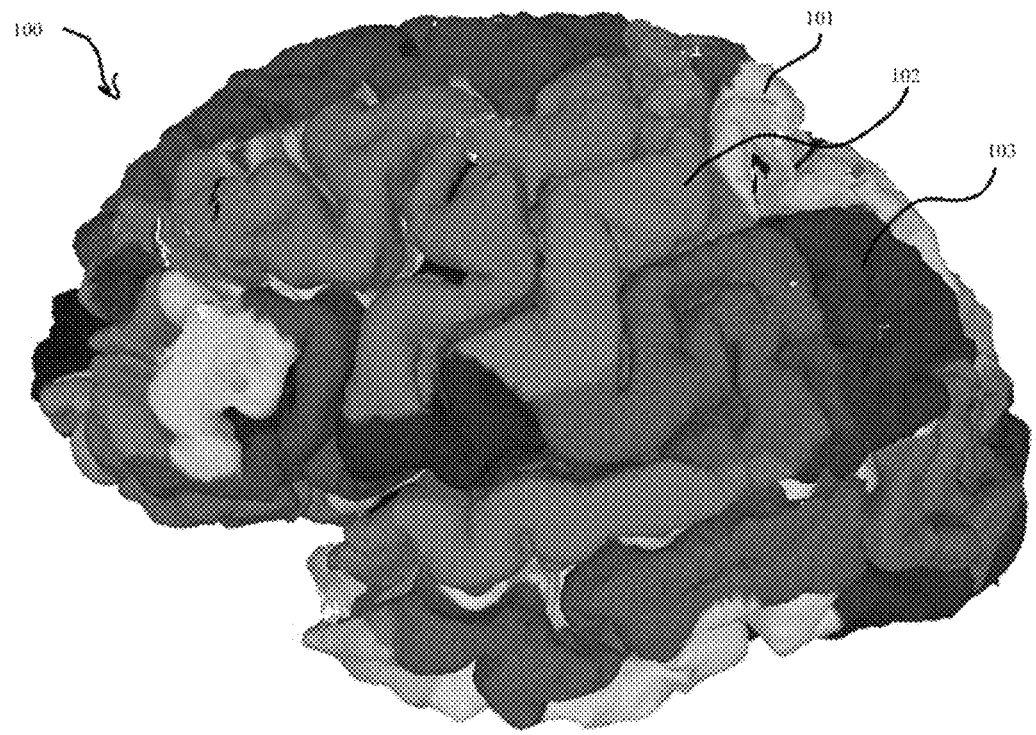
FIG. 1 illustrates an example of 3D cortical model of a brain which may be parcellated.

The detailed description set forth below is intended as a description of the presently exemplified methods, devices and compositions provided in accordance with aspects of the present invention, and is not intended to represent the only forms in which the present invention may be practiced or utilized. It is to be understood, however, that the same or equivalent functions and components may be accomplished by different embodiments also intended to be encompassed within the spirit and scope of the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the exemplified methods, devices and materials are now described.

The present invention relates to methods for localization and visualization of implanted electrodes, such as, for example, subdural electrodes (SDEs) and depth electrodes (DEs), particularly to localizing and visualizing implanted electrodes to the cortical surface and/or particular volumes of a patient's brain, and more particularly to methods of accurately mapping implanted electrodes to the cortical topology and/or associated topological volumes of a patient's brain. This invention further relates to methods of surgical intervention utilizing accurate cortical surface modeling and/or topological volume modeling of a patient's brain for placement of electrodes and/or utilization thereof for surgical intervention, such as for accurately placing electrodes for optimal recording of electrical signals and/or properly identifying sites for surgical intervention.

In general, accurate and precise localization of electrodes is essential for the interpretation of data from intracranial electro-corticographic (ECoG) recordings. Various physiological issues, such as, for example, blood and fluid accumulation underneath the craniotomy flap, may lead to a non-linear deformation of the brain surface and of an electrode array on post-operative CT scans, and may adversely impact the accurate localization of electrodes located underneath the craniotomy. Prior methods that localize electrodes based on their identification on a post-implantation CT, with co-registration to a pre-implant MRI may further result in significant problems with accuracy of the electrode localization.

The precise localization of implanted electrodes is also generally essential both for clinical purposes as well as for research purposes, such as, for example, in integrating estimates from other imaging data sets like functional MRI (fMRI), positron emission tomography (PET), single photon emission computed tomography (SPECT) and/or magneto-encephalography (MEG). Additionally, the growing field of neural prosthetics also depends very greatly on precise estimates of where in the brain data is being collected from, or where stimulation for neuromodulation is being delivered. The precise placement of probes for sampling or providing biologic or chemical materials into the brain is also dependent on the delineation of cortical targets and optimization of trajectories (akin to those use for DE placement) to attain maximal coverage/sampling with minimal risk of vascular injury.

Implantation of SDEs in patients with pharmaco-resistant epilepsy is a common strategy in epilepsy surgery that is employed when there is no discrete electro-physiologically abnormal lesion. To properly plan the cortical resection, precise electrode locations are generally needed to determine the proximity of the seizure focus relative to well-established anatomic or functional landmarks. Beyond this, accurate electrode localization is generally crucial to the process of integrating intracranial electrophysiological data with other imaging techniques used to map out the epileptogenic network such as localization of inter-ictal spikes by magneto-encephalography (MEG), measurements of aberrant cerebral blood flow and metabolism with SPECT or PET. Furthermore, accurate localization allows for the identification of eloquent cortical regions, and functional localization data, principally from functional MRI (fMRI) and MEG recordings overlaid onto the pre-surgical MRI scans. These data sets are essential prior to some resections and need to be precisely co-registered onto the individual patient's brain volume for comparison with the findings from the SDE recordings. In addition, there is a growing interest in the use of SDE-based intracranial ECoG data to provide unique insights into cerebral networks involved in motor function, language, and cognitive control. Individual and grouped analyses of these data rely on precise electrode localization due to the co-registration of data between subjects.

A great variety of strategies have been implemented to represent the electrodes onto a volumetric representation of the brain. Most of these, however, do not consider the effect of the shift and rely on the artifact of the electrodes produced on post-implantation X-rays, CT scans, or MRIs to give a close approximation of where the electrodes are. While useful as crude approximates, such methods may generally be untenable for the applications discussed above.

In general as disclosed herein, precise localization as well as optimized viewing of implanted intracranial electrodes may be shown on a manipulable 3D cortical mesh model that may be parcellated, such as by automatic manipulation, to show anatomic details of specific brain regions (e.g. cortical gyri), such as where the electrodes are placed. Thus, both precise localization as well as optimized viewing of implanted intracranial electrodes may be accomplished. In various embodiments, the 3D cortical model may be generated by, among other methods, performing anatomical MRI (aMRI) scans of a patient's brain and utilizing modeling software. For example, FreeSurfer type software may be utilized to construct a 3D pial cortical surface from the aMRI scans, which may further be visualized using SUMA (Surface Mapping) type software. SUMA (Surface Mapping) is a program that adds cortical surface based functional imaging analysis to the AFNI suite of programs. AFNI is a set of C programs available from National Institute of Mental Health for processing, analyzing, and displaying functional MRI (FMRI) data—a technique for mapping human brain activity. SUMA allows the viewing of 3D cortical surface renderings, the mapping of volumetric data onto them and, in other incarnations can be used to perform surface based computations and statistical inferences. Parcellation of the 3D cortical model to show additional anatomical features, such as individualized parcellated cortical surface, color coded to depict individual gyri and sulci, may be accomplished, for example, using the 'Destrieux' atlas in conjunction with FreeSurfer. In general, other proprietary software and/or formats may also be employed, such as, for example, those that allow for increased ease of user interaction with the imaging data, allow for user defined settings to be easily implemented and for greater flexibility in the resolution at which the pial mesh models and other surfaces such as smoother or coarser pial envelopes and gray white matter interfaces are generated.

FIG. 1 illustrates an example of 3D cortical model of a brain 100 which may be parcellated, as illustrated, to show specific brain regions, such as the illustrated cortical gyri highlighted as different shaded regions, for example with gyri 101, 102 and 103. The parcellation may generally be displayed in a graphical manner utilizing any appropriate delineation of regions, such as by color coding, shading, texture, and/or any other appropriate markup.

For example, the mesh model may be morphed into unnatural shapes, such as, for example, a dilated, smoothed pial surface, that may allow for viewing the areas that individual electrodes are in contact with, as well as the regions where such recording/stimulation is not happening, thus providing a holistic view of the data. Further, the localization of electrodes onto an individually parcellated cortical surface may allow for the a priori assignment of putative functional zones relative to each electrode. This may, for example, augment, verify or altogether replace imaging based functional mapping techniques (e.g. MEG or fMRI) in some cases, and/or electrical cortical stimulation mapping in others.

Another consideration in the visualization of electrodes on a cortical surface is the determination of cortical area that is recorded by each electrode, and the assessment of the ⅔ of remaining cortex that is "buried" beneath the surface. Further in general, more holistic representations of the brain may be utilized, such as, for example, to illustrate relationships at electrodes to the entire cortex, including "buried" or "unburied" surface features. For example, it is generally known that subdural grid electrodes only sample from gyral crowns and not from the intervening sulci or from buried cortex such as the insula. The pial mesh model of the brain may thus be morphed into a "lissencephalic" view of the entire cortex. This process essentially flattens the difference between the depths of the sulci and the peaks of the gyri, while still preserving the overall shape of the brain.

Figure 2:
FIG. 2 illustrates an example of a flattened "lissencephalic" view of the entire cortex.
Figure 2A:
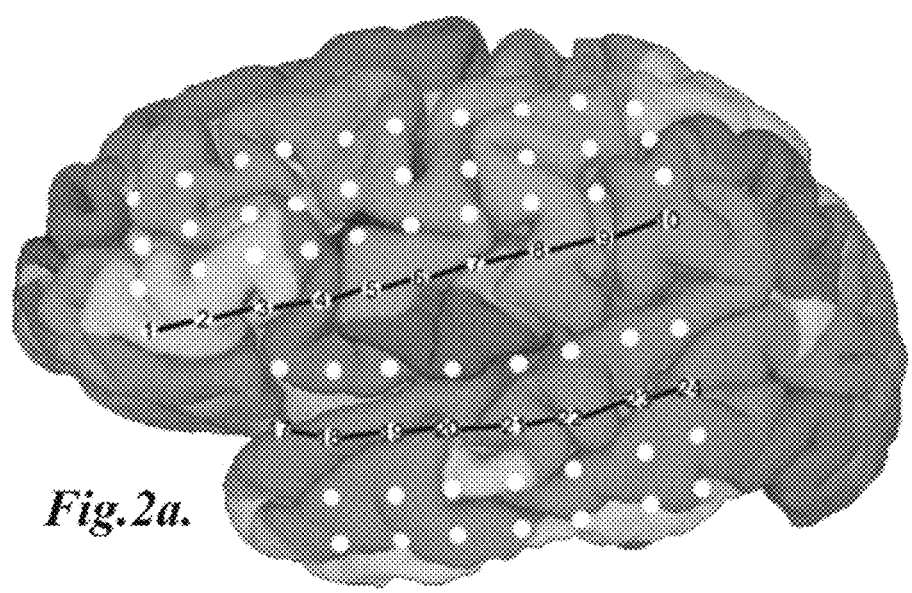
FIGS. 2a and 2b illustrate 3D cortical models that have been parcellated and lissencephalically parcellated, respectively, each showing the implantation of a series of electrodes.
Figure 2B:
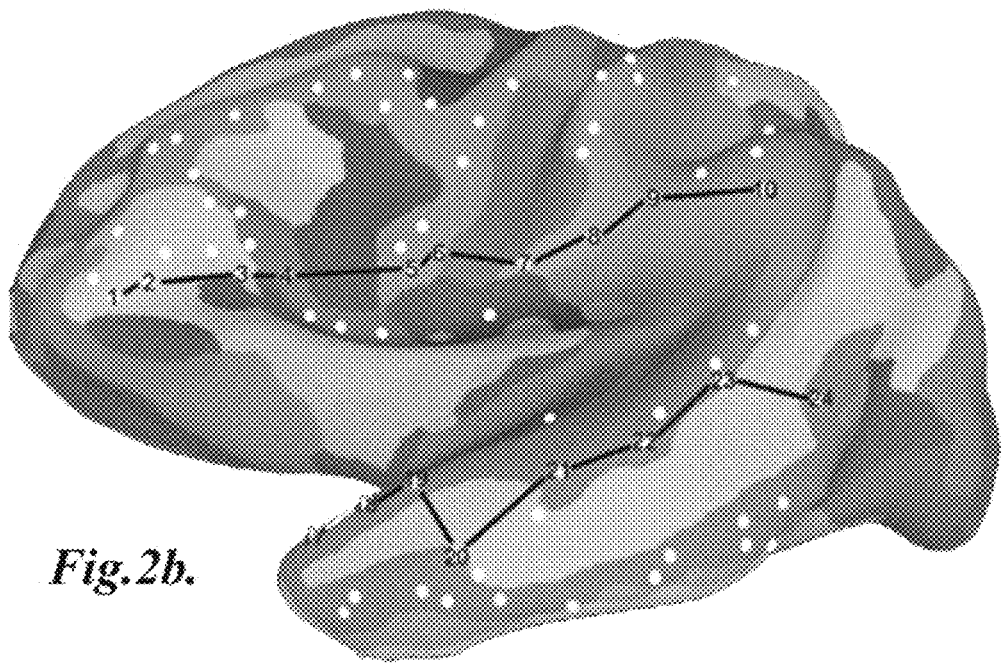

FIG. 2 illustrates an example of a flattened "lissencephalic" view of the entire cortex 200 with darker gray regions 201 illustrating gyri and lighter gray regions 202 illustrating sulci while retaining the overall general shape of the brain in the representation. This shows how apparently adjoining "unburied" regions may have large amounts of gray matter intervening between them, which could be factored into the interpretation of data from them, such as regarding seizure onset zones as well as functional mapping data. This may further be illustrated in FIGS. 2a and 2b, which illustrate 3D models that have been parcellated and lissencephalically parcellated, respectively, each showing the implantation of a series of electrodes (white dots). The upper panel shows a patient's pial surface with both a frontal and a temporal grid represented. The automated parcellation process outlines edges between particular sulci and gyri, which may be represented using different color coding, shading, texturing and/or any other appropriate markup. The parcellation scheme illustrated in FIG. 2b shows the dilated lissencephalic pial surface with the electrodes still placed in their anatomical positions as in FIG. 2a in the natural space that are then transformed along with the surface dilation, the Euclidian distance being illustrated in FIG. 2a with the connecting black lines and the dilated distance being illustrated in FIG. 2b. This shows how apparently adjoining electrodes may have large amounts of gray matter intervening between them, which could be factored into the interpretation of data from them regarding seizure onset zones as well as functional mapping data.

In one aspect of the present invention, a method for localization and/or visualization of implanted electrodes on a patient's brain includes utilizing visual registration of electrodes in relation to anatomical features, such as, for example, cortical surface anatomy. In general, a three-dimensional (3D) cortical model of the patient's brain may be generated, such as by utilizing an anatomical magnetic resonance imaging (MRI) study, and/or any other appropriate method, such as those discussed above. For example, a 3D cortical model of the patient's brain may further generally include gyral and sulcal anatomical features of the brain, parcellation and visual representation of individual features, and/or any other desired anatomical features which may be included with a particular scanning and/or imaging method, such as discussed in general above.

Figure 3A:
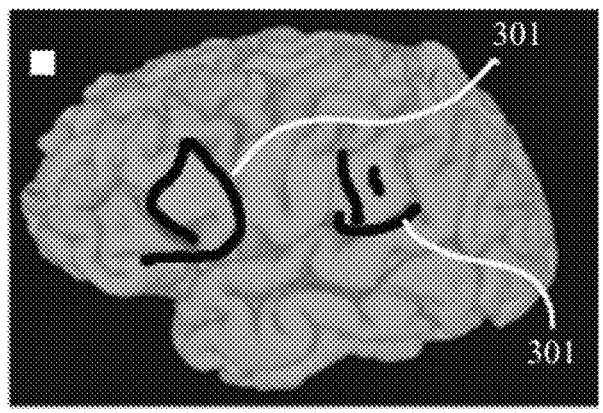
FIGS. 3a, 3b and 3c illustrate examples with 4 different brains of utilizing intraoperative imaging in conjunction with a 3D cortical model for mapping the locations of implanted electrodes.
Figure 3B:
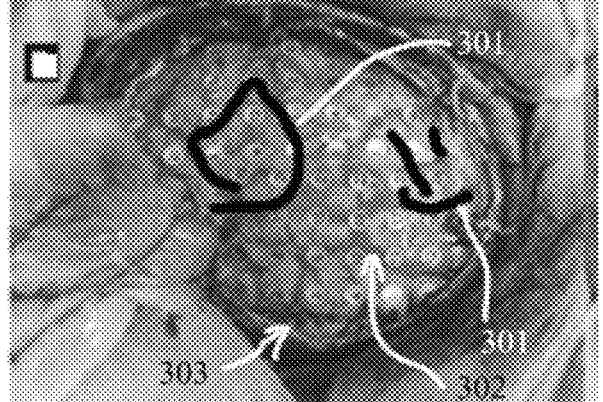
Figure 3C:
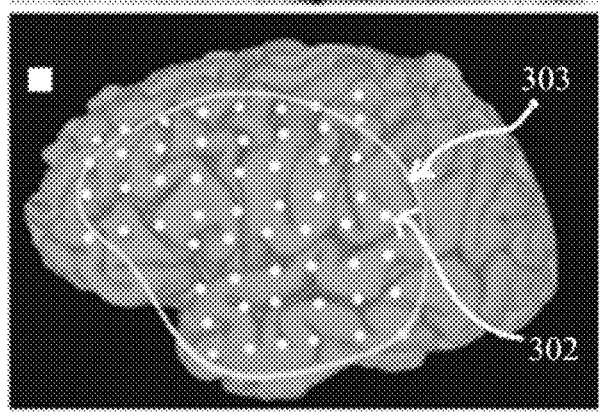

In some exemplary embodiments, the visual registration of implanted electrodes may utilize pre-implantation and post-implantation imaging of the brain in an electrode array implantation, such as by utilizing digital and/or analog photography of the operative site in an operating room (OR). FIGS. 3a, 3b and 3c illustrate examples with a brain of utilizing intraoperative imaging in conjunction with a 3D cortical model for mapping the locations of implanted electrodes.

Pre-implantation imaging may generally provide visual information of the underlying cortical surface prior to implantation of the electrodes and may thus be utilized to compare anatomical features with the 3D cortical model, such as to establish anatomical landmarks, as illustrated in FIG. 3a with anatomical landmarks shown as black lines 301 on the 3D cortical model. After implantation of the electrodes, post-implantation imaging may be performed to visualize the electrodes 302 and the anatomical features of the brain, as illustrated in FIG. 3b showing the anatomical landmarks 301 from FIG. 3a in a post-implantation photograph, as well as the craniotomy boundary 303. In one embodiment, a skilled practitioner, such as, for example, a physician or veterinarian, may readily compare the anatomical features from the intraoperative imaging to the 3D cortical model, such as by matching and/or aligning anatomical landmarks, to visually translate the locations of the electrodes from the intraoperative imaging to the 3D cortical model. FIG. 3c illustrates examples of the yielded locations of the electrodes 302 using intraoperative photography and comparison to the anatomical landmarks on the 3D cortical models (the craniotomy boundary 303 is illustrated). The localization of the electrodes on the 3D cortical model may then be employed to determine useful electrocorticographic (ECoG) information from the patient.

In another aspect of the present invention, a method for localization and/or visualization of implanted electrodes on a patient's brain includes utilizing visual registration of a set of electrodes in relation to anatomical features, such as, for example, cortical surface anatomy, and utilizing modeling to recursively determine the locations of the remaining electrodes relative to the anatomical features. In general, a three-dimensional (3D) cortical model of the patient's brain may be generated, such as by utilizing an anatomical magnetic resonance imaging (MRI) study, and/or any other appropriate method, such as those discussed above. The 3D cortical model of the patient's brain may further generally include gyral and sulcal anatomical features of the brain, parcellation and visual representation of individual features, and/or any other desired anatomical features which may be included with a particular scanning and/or imaging method, such as discussed in general above. A further 3D model may also be generated which may generally omit the sulcal anatomical features, thus omitting the "buried" portion of the cortical surface from the model. This "smoothed" 3D model may be utilized, for example, to aid in recursively registering the locations of the electrodes on the unburied cortical surface. This may generally be desirable as the implantation of electrode arrays on the pial surface does not involve placement of any electrodes or other portions of the array directly into an sulcal formations and thus only on the gyral crowns.

In some exemplary embodiments, the visual registration of a set of implanted electrodes, such as selected set among a group of electrodes, may utilize pre-implantation and post-implantation imaging of the brain in an electrode array implantation, such as by utilizing digital and/or analog photography of the operative site in an OR. Pre-implantation imaging may generally provide visual information of the underlying cortical surface prior to implantation of the electrodes and may thus be utilized to compare anatomical features with the 3D model, such as to establish anatomical landmarks. After implantation of the electrodes, post-implantation imaging may be performed to visualize the electrodes and the anatomical features of the brain. In one embodiment, a skilled practitioner, such as, for example, a physician or veterinarian, may readily compare the anatomical features from the intraoperative imaging to the 3D model, such as by matching and/or aligning anatomical landmarks, to visually translate the locations of the electrodes from the intraoperative imaging to the 3D model.

In general, electrodes to be visualized and localized by the skilled practitioner may be selected for their value in aiding determination of the locations of the other electrodes in an array, and the electrodes to be visualized and localized by the skilled practitioner may further be regarded as reliable reference points for localizing the remaining electrodes in relation to them.

In some embodiments, the electrodes may generally be implanted as a grid of electrodes with predetermined locations and/or dimensions on a substrate such that only a set of the electrodes may need to be localized and the remaining electrodes may be localized by extrapolating based on distance and/or relative position from the known electrodes. For example, a grid of electrodes may be present on a substrate in a square grid pattern with known dimensions and distance between grid points. For further example, a common grid pattern of SDEs employs a 1×1 cm square grid arrangement.

In some exemplary embodiments, the corner electrodes of a grid may be visually registered via intraoperative imaging, as discussed above, and then utilized to recursively localize the remaining electrodes to the cortical surface by partitioning the grid ("recursive grid partitioning"). FIGS. 4*a*, 4*b*, 4*c* and 4*d* illustrate a visualization of an example of recursive grid partitioning utilizing a square grid of 1×1 cm placed electrodes in an array. In one embodiment, the corner electrodes may generally be present close to the boundaries of the craniotomy flap and visually registered to a smoothed 3D model, such as a 3D pial surface model which may generally omit the sulcal buried portions of the cortical surface, as illustrated in FIG. 4*a* with the white dots illustrating the corner electrodes. This may be desirable as the electrodes may generally only be implanted onto the surface unburied portions and the intervening substrate of the electrode grid may conform to the unburied contours of the pial surface, but not to the buried contours of the cortical surface. Utilizing modeling methods, the known inter-electrode distances between the corner electrodes may then be contoured to the non-linear pial surface in the smoothed 3D model and the remaining electrodes may be localized along the contoured lines. FIG. 4*a* illustrates (black lines) the connecting lines contoured to the pial surface in the modeling software. Coordinates of the 4 corners of the grid from visible parts/ CT artifacts may be chosen based on the intraoperative photograph compared with a 3D pial mesh model generated using a high-resolution MRI image. Lines as illustrated are generated on the 3D cortical surface connecting these locations. This grid may then be portioned repeatedly until the software arrives at the appropriate numbers of rows and columns. Electrodes may then be localized to the centers of grid intersections to complete the process, as illustrated with the electrodes (white dots) being placed at the grid intersections (black line intersections) in FIGS. 4*c* and 4*d*. Thus the entire electrode grid may be contoured onto the smoothed 3D model to recursively yield the localized electrodes on the pial surface. This may be particularly desirable to localize electrodes which are not readily visible, such as those placed beyond the craniotomy flap, as their locations may be recursively determined using visible electrodes within the craniotomy flap region. The localization of the electrodes on the smoothed 3D model may then be aligned with the unsmoothed 3D cortical model to map the electrodes to determine useful ECoG information from the patient. In other embodiments, reference electrodes may also be selected due to ease of visual localization by the skilled practitioner, such as, for example, due to better viewing ability or proximity to readily identifiable anatomical landmarks.

In general, other grid patterns besides square grids may also be utilized where a finite set of points in the grid may be utilized determinatively to extrapolate the other points of the grid once contoured to a 3D surface model.

In yet another aspect of the present invention, implanted DEs and electrical signals recorded by them may be mapped to a parcellated 3D model of the brain to more accurately determine the particular region(s) of the patient's brain contributing to a particular signal at a DE and/or a portion thereof. In some exemplary embodiments, imaging may be employed prior to implantation of DEs to generate the 3D model of the brain, followed by imaging after implantation of the DEs. The pre-implantation and post-implantation imaging may then be co-registered to localize the DEs in the 3D model of the brain volume, which may then be utilized to show interactions between the DEs and surrounding regions of the brain, such as by using parcellated views of the 3D model. For example, depending on the angle and location of insertion, a DE may interact with multiple distinct anatomical formations which may be visualized with the parcellated 3D model. FIGS. 5a, 5b and 5c illustrate an example of localization of DEs onto a cortical surface map. High resolution CT scans in FIG. 5a and MRI scans may be obtained and co-registered, as illustrated in FIG. 5b. In some embodiments, MRI scans may be utilized for post-implantation scans, such as, for example, when utilizing MRI-compatible electrodes. Modeling software may then be utilized to depict individual recording electrodes on a parcellated cortical surface as shown in FIG. 5c. In some embodiments, the parcellated cortical surface may also be at least partially transparent when displayed to aid in showing the placement of the entire DE within the brain volume. The important vascular structures that need to be localized and preserved during the placement of the probes or electrodes may also be co-localized using a contrasted MRI or CT scan or a MR angiogram or a CT angiogram and depicted together with the pial mesh models. This embodiment would allow for the preservation of these structures while placing the probes/electrodes with precision.

In other embodiments, precision-guided insertion of DEs may also be utilized, such as utilizing robotic insertion and/or other forms of trajectory guided insertion, such that pre-implantation scans may be sufficient to calculate the locations of the DEs post-implantation without additional imaging.

Figure 6:
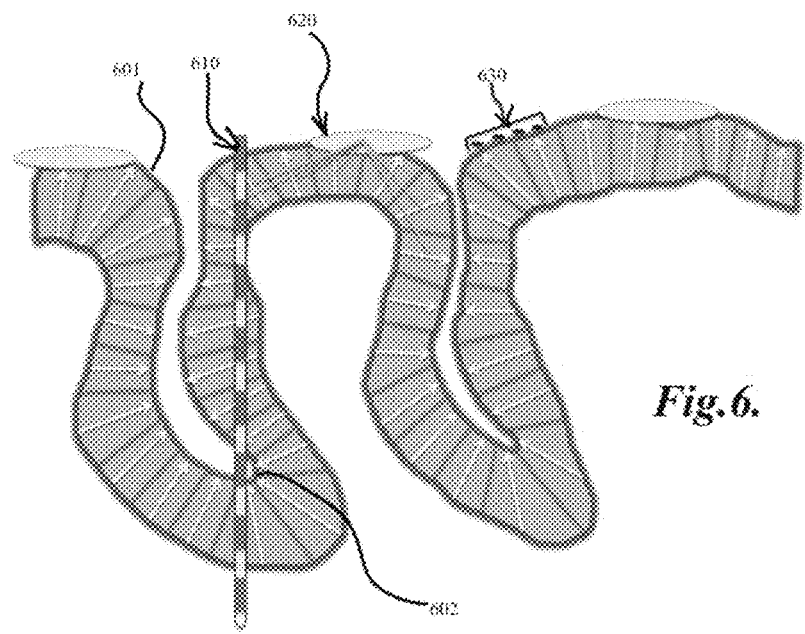
FIG. 6 illustrates the interactions of various electrode types with a portion of the cortical anatomy.

This may be desirable as DEs may interact in various ways with the cortical anatomy. For example, FIG. 6 illustrates the interactions of various electrode types, such as DE 610, SDE 620 and micro SDE 630, with a portion of the cortical anatomy, such as gyri 601 and sulci 602.

In still another aspect of the present invention, electrical signals from implanted electrodes may be mapped to the 3D cortical surface to more accurately determine the particular region(s) of the patient's brain contributing to a particular signal at an electrode. In general, traditional methods typically map electrical activity at an electrode to regions of the brain which are closest in Euclidian distance to the electrode which, without being bound to any particular theory, may erroneously attribute electrical activity to topologically distant portions of the brain due to the Euclidian distance not accounting for surrounding topology about the electrode. FIGS. 7a-7c and 8a-8c illustrate an example of a traditional Euclidian distance expansion from an electrode location compared to an expansion accounting for the underlying topology surrounding the electrode.

Figure 7A:
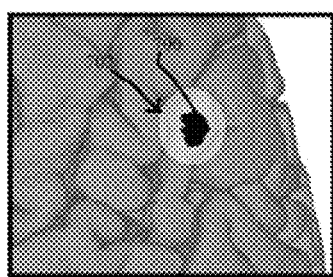
FIGS. 7a-7c and 8a-8c illustrate an example of a traditional Euclidian distance expansion from an electrode location compared to an expansion accounting for the underlying topology surrounding the electrode.
Figure 7B:
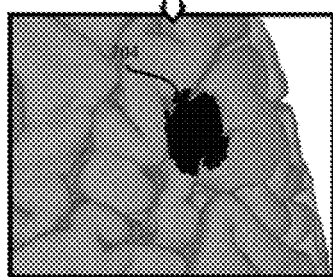
Figure 7C:
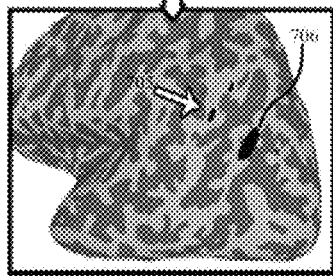
Figure 8A:
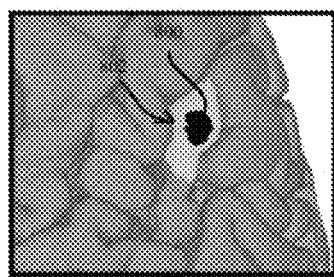
Figure 8B:
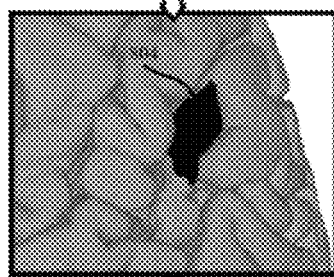
Figure 8C:
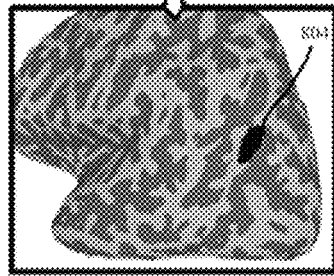

In some exemplary embodiments, signal activity from implanted SDEs may be represented on a 3D cortical model to illustrate regions that may be contributing to the activity utilizing methods that account for surrounding topology around the SDEs. In general, the folded nature of the cortical surface may contribute to falsely contributing activity at an SDE to topologically distant regions, which may be distinct anatomical structures despite being situated close in Euclidian space, as illustrated with the region of interest 700 being expanded to area 702 in Euclidian space to form area 704 in FIGS. 7a and 7b, and as visualized with the flattened representation in FIG. 7c showing topologically distant regions 705 and 706 being attributed to activity at the electrode. To aid accounting for the underlying topology of the brain surrounding an SDE, the recording area around the electrode may be projected geodesically onto the surface 3D cortical model such that buried portions of the cortical surface are accounted for in attributing a region to activity at the SDE, as illustrated in FIGS. 8a, 8b and 8c. FIG. 8a illustrates a region of interest 800 expanded on the cortical surface using geodesic expansion 802 to yield area 804. Comparing the Euclidean distance expansion in FIGS. 7a-7c vs. the using the geodesic growth approach in FIGS. 8a-8c for a given electrode, the Euclidean technique (currently the standard) creates a region of interest that falsely includes topologically distant regions (705 and 706 in FIG. 7c) that are close in space but not connected to the electrode. Geodesic growth along the pial surface includes only nodes contiguous with the area the electrode is in contact with, as shown in FIG. 8c with contiguous area 804. The geodesic projection may further incorporate any desirable decay function to represent the activity signal from the recording area of the SDE. This approach may also be extended to physical models that represent the spread of drugs or chemicals instilled into the brain to occur along preferred diffusion pathways in the white or gray matter of the brain.

For further example, this method for visualizing electrodes on an inflated surface has dynamic clinical implications. Determination of the cortical area influencing a specific electrode, in the context of the gyral crowns and the sulcal anatomy between them, in a quick and accurate manner is paramount to the proper planning and determination of boundaries used in the resection of epileptogenic tissue. This visualization helps ensure that as much healthy brain tissue as possible remains intact, and that unnecessary procedures are not undertaken. This method also provides, for example, a sense of the cortical surface not sampled by the electrode, and the potential roles this "electrophysiologically hidden" cortex may play in both eloquent functions and in seizure onsets.

In another aspect of the present invention, various forms of 3D modeling of the cortical surface may be utilized to guide placement of electrodes and/or to generate customized electrode arrays. In some embodiments, a 3D cortical model may be utilized to guide the location and/or orientation of electrodes, such as in arrays, such as to optimize particular desired recording regions of electrodes over areas of interest. In still other embodiments, 3D cortical models may be utilized to guide placement of an electrode array using a smaller craniotomy opening. In yet other embodiments, customized electrode arrays may be designed to conform to the particular anatomical features and/or needs for a patient by utilizing the patient's specific 3D cortical model prior to any electrode implantation. In some embodiments, 3D printing and/or other forms of rapid manufacturing may be utilized to create customized electrode arrays based on the cortical anatomy considerations drawn from a patient's 3D cortical model. This may be desirable, for example, to aid in placing electrodes in desired areas and/or to avoid placement in anatomically ambiguous locations, such as between gyri or lobes.

Example of or Photo Localization of Electrodes

Utilizing OR photographs in relation to the cortical surface anatomy yields highly accurate localization of implanted electrodes. These electrodes are properly localized as they are easily visualized in their final locations in photographs. Prior approaches of this type have used surface blood vessels from the OR pictures and MR venograms of the brain to co-register data onto 3D volumetric renderings of the brain. These approaches are tedious and also prone to errors intrinsic to the co-registration of imaging datasets. The 3D pial mesh model allows for a very realistic depiction of the cortical surface that can easily be compared with the cortical landmarks as visualized in an OR photograph and there are no issues of co-registration.

To determine the exact locations of the electrodes as they should lie on the surface of the brain, the cortical landmarks underneath the electrode grids were visualized using OR photographs. This cortical anatomy was aligned with the high-resolution pial surface in SUMA. FIGS. 3a, 3b and 3c show four examples of 3D cortical surface renderings of four different patients, with gyral and sulcal landmarks that provide the connection between the 2D photograph and the 3D surface volume. When they were properly aligned, the photograph was overlaid to the surface with high-resolution sulcal and gyral anatomy. FIG. 4b shows four OR photographs of the brains in FIG. 4a with the same landmarks after implantation of subdural electrodes. It can be seen that the landmarks in (A) match with those in (B), where target electrodes' localizations in each of the patients are compared with corresponding electrodes in the explant photograph from the OR. It then became possible to make a visual translation between where the electrodes were located based on the operating room photos and where they should be located on the cortical surface. FIG. 4c shows the precise locations of the implanted electrodes in relation to the cortical surface anatomy. As illustrated in FIG. 4c, the final locations can be easily visualized on the high resolution 3D cortical surface. The yellow line marks the boundary of the craniotomy, and blue lines mark the prominent sulci and cortical landmarks used to match the photograph to the cortical surface model.

Given that a small degree of shift can occur in electrode position after the closure of the dura, we obtained photographs in all cases both at the time of electrode implantation and at the time of re-opening the craniotomy for electrode explanation and resection. This localization method, though operator effort and time intensive, provides a "gold standard" to which all other localization techniques can be compared.

The localization of electrodes using the surface anatomy from the OR pictures as compared to the 3D cortical surface is exceedingly accurate, but a tedious process. This can be considered a gold standard because it can be easily validated that these electrodes are in their proper location, as they are easily visualized with high-resolution photographs. This method is not subject to co-registration errors such as the localization using cortical veins. Given its high accuracy, this method is preferred. For clinical purposes, this degree of accuracy may not always be necessary, and the photo-localization technique may be applied selectively to more precisely localize electrodes of critical interest.

Example of Recursive Grid Partitioning Localization of Electrodes

This method relies upon the OR photographs similar to the OR photo localization method above. This method utilizes the operating room photographs and the 3D cortical model of the brain. Specifically, similar to the OR photo localization method described above, electrodes are identified at the visible corners of each grid using the surface landmarks in the photographs. The process of electrode localization therefore begins with four surface coordinates picked from OR photos. The identified electrodes are positioned onto the cortical surface in SUMA using sulcal and gyral landmarks. FIGS. 4a, 4b, 4c and 4d show the coordinates of the 4 corners of the grid which are picked out based on the OR photo compared to a 3D pial mesh model generated using a high resolution T1 weighted image.

Next, an enveloped pial cortical surface with the same size and dimensions of the pial surface, but excluding the sulcal anatomy, was created using the FreeSurfer package. The four sets of electrode coordinates, the 3D pial surface, and the 3D pial envelope ("smoothed" 3D model excluding the sulcal anatomy) were all then imported into MATLAB. Software then automatically connected these four electrode locations with curved lines along the pial envelope surface. Specifically, a custom MATLAB script was used to create lines on the 3D cortical surface connecting these locations. This grid was then portioned repeatedly until the program arrives at the appropriate numbers of rows and columns. Electrodes were then localized centered at grid intersections to complete the process. In this example, based on the known dimensions of the grid that was implanted, the rectangular surface was recursively partitioned into a grid with 1×1 cm spacing, which corresponds to the inter-electrode distances in the array. The list of coordinates corresponding to the closest node adjoining intersection points on the grid were compiled and then used to place spheroids denoting those electrodes both in MATLAB and in SUMA.

Figure 4E:
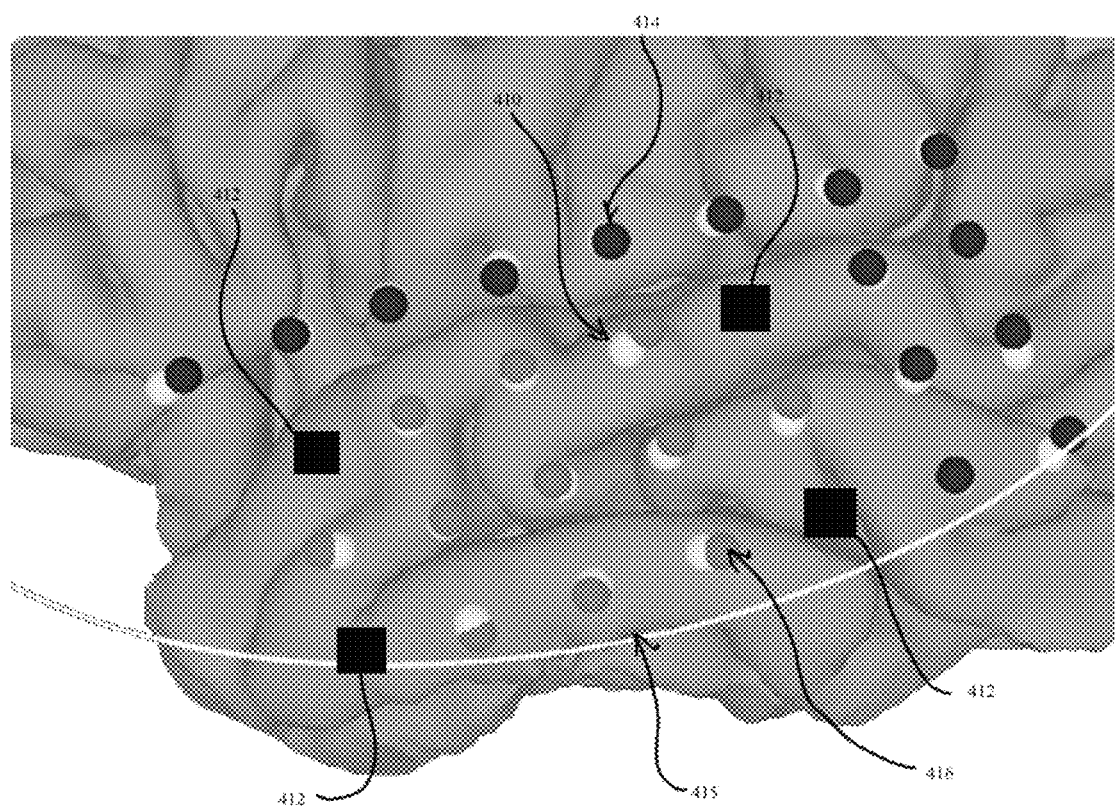
FIG. 4e illustrates a visualization of an example of recursive grid partitioning with an interior set of electrodes.

For grids that are partially visible and partially tucked under the edge of the craniotomy, the same method was applied; however, the seeding of initial points was done with four electrodes at the edges of the visible portion of the electrode array. By extrapolating out along the pial surface using the grid dimensions, it was possible to accurately localize electrodes not visible in the OR photograph. To evaluate the accuracy of such extrapolation, the electrodes on a grid that were completely visible were localized, but used seed points of 4 electrodes from an interior portion of the grid rather than the four corners, and used them to localize the rest of the array. This extrapolation technique is illustrated in FIG. 4e. The results of this approach were cross-validated with those from direct localization of these electrodes using the OR photographs to test the accuracy of this technique. On a grid entirely visible through the craniotomy, the boundary shown as white line 415, a subset of electrodes (black squares 412) were chosen and localized on the pial surface using anatomical landmarks. Intervening electrodes (gray circles 416) were localized and used to extrapolate the "non-visible" electrodes (black circles 414). Given that these electrodes are in fact visible on the OR photo, their estimated locations could be compared to their actual ones, shown as white circles 410. The average error of electrodes in green was 1.75 mm and of the electrodes in blue was 1.99 mm.

The recursive grid partitioning method provides the lowest the error we have seen from all performed methods. Of the 672 electrodes that we localized using this technique, there was a maximum error of 6.39 mm with a mean error of 1.97 mm. This mean does not include the four corner electrodes from every grid we used as a starting point to generate the matrix. Though this method does not decrease the error to zero, it does allow the smallest error of methods we know of (p<10-18) in the most time efficient manner. A visual analysis of this method did not seem to show a trend towards picking locations that are consistently skewed in any particular direction.

Although the invention has been described with respect to specific embodiments thereof, these embodiments are merely illustrative, and not restrictive of the invention. The description herein of illustrated embodiments of the invention, including the description in the Abstract and Summary, is not intended to be exhaustive or to limit the invention to the precise forms disclosed herein (and in particular, the inclusion of any particular embodiment, feature or function within the Abstract or Summary is not intended to limit the scope of the invention to such embodiment, feature or function). Rather, the description is intended to describe illustrative embodiments, features and functions in order to provide a person of ordinary skill in the art context to understand the invention without limiting the invention to any particularly described embodiment, feature or function, including any such embodiment feature or function described in the Abstract or Summary. While specific embodiments of, and examples for, the invention are described herein for illustrative purposes only, various equivalent modifications are possible within the spirit and scope of the invention, as those skilled in the relevant art will recognize and appreciate. As indicated, these modifications may be made to the invention in light of the foregoing description of illustrated embodiments of the invention and are to be included within the spirit and scope of the invention. Thus, while the invention has been described herein with reference to particular embodiments thereof, a latitude of modification, various changes and substitutions are intended in the foregoing disclosures, and it will be appreciated that in some instances some features of embodiments of the invention will be employed without a corresponding use of other features without departing from the scope and spirit of the invention as set forth. Therefore, many modifications may be made to adapt a particular situation or material to the essential scope and spirit of the invention. The disclosures of all patents, patent applications and publications cited herein are hereby incorporated herein by reference in their entireties, to the extent that they are consistent with the present disclosure set forth herein.

Reference throughout this specification to "one embodiment", "an embodiment", or "a specific embodiment" or similar terminology means that a particular feature, structure, or characteristic described in connection with the embodiment is included in at least one embodiment and may not necessarily be present in all embodiments. Thus, respective appearances of the phrases "in one embodiment", "in an embodiment", or "in a specific embodiment" or similar terminology in various places throughout this specification are not necessarily referring to the same embodiment. Furthermore, the particular features, structures, or characteristics of any particular embodiment may be combined in any suitable manner with one or more other embodiments. It is to be understood that other variations and modifications of the embodiments described and illustrated herein are possible in light of the teachings herein and are to be considered as part of the spirit and scope of the invention.

In the description herein, numerous specific details are provided, such as examples of components and/or methods, to provide a thorough understanding of embodiments of the invention. One skilled in the relevant art will recognize, however, that an embodiment may be able to be practiced without one or more of the specific details, or with other apparatus, systems, assemblies, methods, components, materials, parts, and/or the like. In other instances, well-known structures, components, systems, materials, or operations are not specifically shown or described in detail to avoid obscuring aspects of embodiments of the invention. While the invention may be illustrated by using a particular embodiment, this is not and does not limit the invention to any particular embodiment and a person of ordinary skill in the art will recognize that additional embodiments are readily understandable and are a part of this invention.

At least a portion of embodiments discussed herein can be implemented using a computer communicatively coupled to a network (for example, the Internet), another computer, or in a standalone computer. As is known to those skilled in the art, a suitable computer can include a central processing unit ("CPU"), at least one read-only memory ("ROM"), at least one random access memory ("RAM"), at least one hard drive ("HD"), and one or more input/output ("I/O") device(s). The I/O devices can include a keyboard, monitor, printer, electronic pointing device (for example, mouse, trackball, stylist, touch pad, etc.), or the like.

ROM, RAM, and HD are computer memories for storing computer-executable instructions executable by the CPU or capable of being complied or interpreted to be executable by the CPU. Suitable computer-executable instructions may reside on a computer readable medium (e.g., ROM, RAM, and/or HD), hardware circuitry or the like, or any combination thereof. Within this disclosure, the term "computer readable medium" or is not limited to ROM, RAM, and HD and can include any type of data storage medium that can be read by a processor. For example, a computer-readable medium may refer to a data cartridge, a data backup magnetic tape, a floppy diskette, a flash memory drive, an optical data storage drive, a CD-ROM, ROM, RAM, HD, or the like. Software implementing some embodiments disclosed herein can include computer-executable instructions that may reside on a non-transitory computer readable medium (for example, a disk, CD-ROM, a memory, etc.). Alternatively, the computer-executable instructions may be stored as software code components on a direct access storage device array, magnetic tape, floppy diskette, optical storage device, or other appropriate computer-readable medium or storage device.

Any suitable programming language can be used to implement the routines, methods or programs of embodiments of the invention described herein, including the custom script. Other software/hardware/network architectures may be used. For example, the software tools and the custom script may be implemented on one computer or shared/distributed among two or more computers in or across a network. Communications between computers implementing embodiments can be accomplished using any electronic, optical, radio frequency signals, or other suitable methods and tools of communication in compliance with known network protocols. Additionally, any signal arrows in the drawings/figures should be considered only as exemplary, and not limiting, unless otherwise specifically noted. Based on the disclosure and teachings provided herein, a person of ordinary skill in the art will appreciate other ways and/or methods to implement the invention.

As used herein, the terms "comprises," "comprising," "includes," "including," "has," "having," or any other variation thereof, are intended to cover a non-exclusive inclusion. For example, a process, product, article, or apparatus that comprises a list of elements is not necessarily limited only those elements but may include other elements not expressly listed or inherent to such process, process, article, or apparatus.

Furthermore, the term "or" as used herein is generally intended to mean "and/or" unless otherwise indicated. For example, a condition A or B is satisfied by any one of the following: A is true (or present) and B is false (or not present), A is false (or not present) and B is true (or present), and both A and B are true (or present). As used herein, including the claims that follow, a term preceded by "a" or "an" (and "the" when antecedent basis is "a" or "an") includes both singular and plural of such term, unless clearly indicated within the claim otherwise (i.e., that the reference "a" or "an" clearly indicates only the singular or only the plural). Also, as used in the description herein, the meaning of "in" includes "in" and "on" unless the context clearly dictates otherwise.

As used herein, "patient" or "subject" includes mammalian organisms, such as human and non-human mammals, for example, but not limited to, rodents, mice, rats, non-human primates, companion animals such as dogs and cats as well as livestock, e.g., sheep, cow, horse, etc. Therefore, for example, although the described embodiments illustrate use of the present methods on humans, those of skill in the art would readily recognize that these methods and compositions could also be applied to veterinary medicine as well as on other mammals.

The invention claimed is:

1. A method for localization of implanted depth electrodes (DE) in a brain of a subject, said method comprising:
   performing a first anatomical scan of said brain;
   generating a three-dimensional (3D) model of said brain using said anatomical scan, said 3D model comprising cortical topological features;
   implanting at least one DE into said brain;
   performing a second anatomical scan of said brain after said implanting, said second anatomical scan elucidating a position and orientation of said at least one DE relative to said brain;
   aligning said first and second anatomical scans;
   visually projecting said position and orientation of said at least one DE on said 3D model using aligning of said first and second anatomical scans;
   further comprising implanting an array of DEs into said brain prior to said second anatomical scan, wherein said at least one DE comprises a member of said array of DEs; and
   recursively localizing said array of DEs on said 3D model by contouring said array of DEs to said cortical topological features in said 3D model relative to said at least one DE, said array of DEs comprising a grid which conforms to a pial surface in situ with said array of DEs placed at known positions relative to said at least one DE, wherein said contouring of said array of DEs to said cortical topological features comprises contouring said array of DEs to a smoothed 3D model which omits sulcal anatomy and which is aligned with said 3D model.

2. The method of claim 1, wherein said first and second anatomical scans are each performed with a scanning modality selected from the group consisting of magnetic resonance imaging (MRI), computerized tomography (CT), and a combination thereof.

3. The method of claim 2, wherein said at least one DE is constructed from MRI- or CT-compatible material(s).

4. The method of claim 1, further comprising highlighting said cortical topological features by parcellation with different visual coding in said 3D model to illustrate interactions of said DE with said cortical topological features.

5. The method of claim 1, further comprising co-registering and depicting said 3D model with additional anatomical information selected from the group consisting of surface blood vessels, deep blood vessels, white matter pathways and tractography data.

6. The method of claim 1, further comprising visually localizing said array of DEs on said 3D model using a correlation of at least one anatomical landmark.

7. The method of claim 6, wherein said array of DEs are visually localized by a human medical practitioner or automatically by a computer.

8. The method of claim 1, wherein said array of DEs comprises a rectangular grid with at least four reference DEs arranged at corners of said rectangular grid.

9. The method of claim 8, wherein said at least four reference DEs are selected from said array of DEs at positions proximal to a craniotomy boundary used to access said brain.

10. The method of claim 9, wherein said array of DEs extends beyond said craniotomy boundary.

11. The method of claim 9, further comprising projecting said craniotomy boundary on said 3D model.

12. The method of claim 1 further comprising generating a lissencephalic view of said 3D model by flattening a difference between depths of sulci and peaks of gyri while preserving the overall shape of said brain and projecting said position and orientation of said at least one DE on said parcellated view of said 3D model.

13. The method of claim 12, further comprising highlighting said cortical topological features in said lissencephalic view to generate a parcellated lissencephalic view with different visual coding of said 3D model and projecting said position and orientation of said at least one DE onto said parcellated lissencephalic view of said 3D model.

14. The method of claim 1, further comprising displaying a recording zone for said at least one DE by geodesic expansion along said cortical topological features in said 3D model centered on said at least one DE.

15. The method of claim 1, wherein said array of DEs comprises a customized array generated to conform to desired locations based on said 3D model.

16. The method of claim 15, wherein said customized array is generated by 3D printing.

17. The method of claim 1, wherein said at least one DE is implanted using a precision-guided method selected from the group consisting of robotic insertion and trajectory-guided insertion.

18. The method of claim 1, wherein said 3D model is displayed as at least partially transparent to illustrate interaction of said at least one DE with a volume of said brain.

* * * * *

UNITED STATES PATENT AND TRADEMARK OFFICE
CERTIFICATE OF CORRECTION

| | |
|---|---|
| PATENT NO. | : 10,149,618 B1 |
| APPLICATION NO. | : 14/656117 |
| DATED | : December 11, 2018 |
| INVENTOR(S) | : Nitin Tandon et al. |

It is certified that error appears in the above-identified patent and that said Letters Patent is hereby corrected as shown below:

In the Specification

In Column 1, Lines 18-21, please delete the paragraph and insert:
--These inventions were made with U.S. Government support under Grant Nos. DA026452, RR024148 and RR024149 awarded by the National Institutes of Health. The government has certain rights in the invention.-- therefor.

Signed and Sealed this
Seventh Day of October, 2025

John A. Squires
*Director of the United States Patent and Trademark Office*